United States Patent
Hafer et al.

(10) Patent No.: US 9,814,797 B2
(45) Date of Patent: Nov. 14, 2017

(54) ACTIVATING VOLATILE DISPENSING DEVICES

(71) Applicant: The Dial Corporation, Scottsdale, AZ (US)

(72) Inventors: Kevin Hafer, Scottsdale, AZ (US); James Clark, Chicago, IL (US); Matthew Freeborn, Scottsdale, AZ (US)

(73) Assignee: Henkel IP & Holding GmbH (DE)

( * ) Notice: Subject to any disclaimer, the term of this patent is extended or adjusted under 35 U.S.C. 154(b) by 447 days.

(21) Appl. No.: 14/138,189

(22) Filed: Dec. 23, 2013

(65) Prior Publication Data

US 2014/0183274 A1 Jul. 3, 2014

Related U.S. Application Data (60) Provisional application No. 61/747,184, filed on Dec. 28, 2012.

(51) Int. Cl.
| | |
|---|---|
| *A61L 9/04* | (2006.01) |
| *A61L 9/12* | (2006.01) |
| *A01M 29/12* | (2011.01) |
| *B65D 17/00* | (2006.01) |
| *A01M 1/20* | (2006.01) |

(52) U.S. Cl.
CPC ........... *A61L 9/127* (2013.01); *A01M 1/2044* (2013.01); *A01M 29/12* (2013.01); *B65D 17/16* (2013.01); *A61L 2209/133* (2013.01); *Y10T 83/9314* (2015.04)

(58) Field of Classification Search
CPC ................. A61L 9/127; A61L 2209/10; A61L 2209/133; A01M 1/2044; A01M 29/12; B65D 17/16; Y10T 83/9314
USPC .......................... 239/44–51.5; 222/80, 81, 83
See application file for complete search history.

(56) References Cited

U.S. PATENT DOCUMENTS

| | | | | |
|---|---|---|---|---|
| 3,587,968 A | * | 6/1971 | Hennart | A61L 9/12 239/309 |
| 5,823,236 A | * | 10/1998 | Kirby | B67B 7/28 141/329 |
| 2010/0314461 A1 | | 12/2010 | Gruenbacher et al. | |

* cited by examiner

*Primary Examiner* — Jason Boeckmann
(74) *Attorney, Agent, or Firm* — Thomas G. Krivulka (57) ABSTRACT

Methods and apparatus are provided for activating a volatile dispensing device. The apparatus includes a puncturing mechanism formed between a first portion and a second portion of an activation arm and the puncturing mechanism being shaped to move laterally to puncture a volatile container as a compressive load is applied to the activation arm through the first and second portions.

8 Claims, 8 Drawing Sheets

ACTIVATING VOLATILE DISPENSING DEVICES

FIELD OF THE INVENTION

The present invention generally relates to a device for activating volatile dispensing devices, and more particularly relates to a device that punctures a volatile container as the volatile container in inserted into an outer housing of a volatile dispensing device.

BACKGROUND OF THE INVENTION

Air fresheners remove or mask unpleasant odors in the air. Some types of air fresheners use oil or water based volatile compositions that contain a fragrance. When the air freshener's volatile composition is exposed to the ambient environment, the volatile composition evaporates over time, and the fragrance is released into the air. Some air fresheners incorporate a wick that distributes the volatile composition to an emanator pad with a larger surface area to promote evaporation. To prevent the volatile composition from evaporating until desired, a cap is often placed over the emanator pad to minimize the pad's exposure to air until it is desirable to activate the air freshener.

Accordingly, it is desirable to control when a volatile container of an air freshener is opened to release the volatile composition. In addition, it is desirable that a user of an air freshener can activate the air freshener by breaking the protective seal of the volatile container with minimal steps. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An apparatus is provided for activating volatile dispensing devices. The apparatus includes a puncturing mechanism formed between a first portion and a second portion of an activation arm and the puncturing mechanism being shaped to move laterally to puncture a volatile container as a compressive load is applied to the activation arm through the first and second portions.

A method is provided for activating volatile dispensing devices. The method includes inserting a reservoir assembly into an outer housing such that a compressive load is generated in an activation arm that causes a puncturing mechanism to move laterally to puncture a volatile container within the reservoir assembly.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

For those air fresheners that use an emanator pad with a large amount of surface area, a cap is less effective due to a higher likelihood that leaks will form between the cap and the pad. Such leaks expose some of the volatile composition to the ambient environment and led to premature evaporation before it is desirable to activate the air freshener. The principles described herein include a system that prevents the emanator pad and the volatile composition from mixing before the air freshener is activated. Such a system prevents the volatile composition from evaporating prematurely and allows a user to activate the air freshener while inserting a reservoir assembly into the air freshener's outer housing.

The principles described herein include a puncturing mechanism formed between a first portion and a second portion of an activation arm and the puncturing mechanism being shaped to move laterally to puncture a volatile container as a compressive load is applied to the activation arm through the first and second portions. The compressive load may be generated as a reservoir assembly that incorporates the activation arm and the volatile assembly is inserted into the air freshener's outer housing. By puncturing the volatile container, the container's volatile composition is released into the assembly's reservoir and comes into contact with the wick. The wick draws the volatile composition in through capillary action and to an emanator pad that distributes the volatile composition across the pad's surface area. As the emanator pad's surface area becomes saturated with the volatile composition, the volatile composition evaporates off of the emanator pad. By puncturing the volatile container automatically as the reservoir assembly is inserted into the air freshener's outer housing, activating the air freshener imposes minimal effort on the user.

Figure 1:
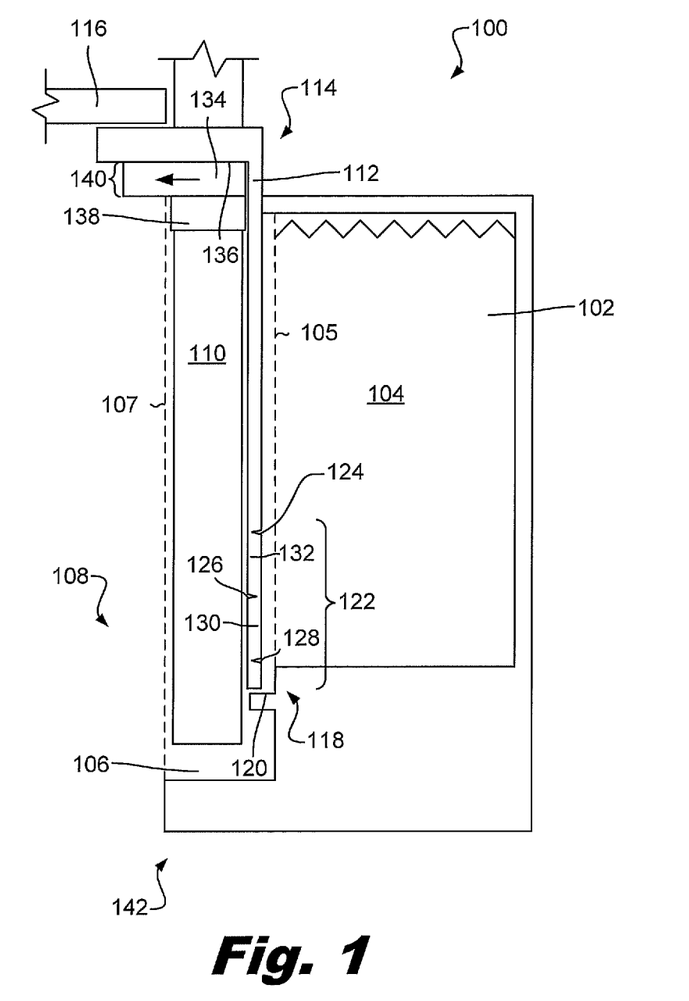
FIG. 1 is a diagram of an example of a reservoir assembly according to the principles described herein.

FIG. 1 is a diagram of an example of a reservoir assembly (100) according to the principles described herein. In this example, the reservoir assembly (100) has a volatile container (102) that contains a volatile composition (104). A portion of the volatile container (102) has a flexible membrane (105) that separates the volatile composition from the remainder of the reservoir (106). A base end (108) of a wick (110) is also positioned with the reservoir. An activation arm (112) is positioned between the volatile container (102) and the wick (110). The activation arm (112) is also shaped such that a first portion (114) of the activation arm (112) will engage an interior protrusion (116) and a second portion (118) of the activation arm (112) will engage a floor (120) of the reservoir (106) when the reservoir assembly (100) is inserted as a single unit into an outer housing, which will be shown and described later in more detail.

The volatile composition (104) may be an aqueous based composition, an oil based composition, another type of composition, or combinations thereof. The volatile composition (104) may include a fragrance, a pesticide, an insecticide, a repellant, an insect repellant, an animal repellant, other volatile compositions, or combinations thereof.

The main body of the reservoir assembly (100) may be made of a plastic that is injection molded, thermoformed, formed with another process, or combinations thereof. In other examples, the main body is made of a metal, another material, or combinations thereof. The flexible membrane (105) is sealed to the main body to form an interior barrier separating the volatile container (102) from the remainder of the reservoir assembly (100). The flexible membrane (105) is made of any appropriate material that is impermeable to the volatile composition and is capable of being punctured with a low force while still having enough strength to retain the weight of the volatile composition (104) within the volatile container (102). For example, the flexible membrane (105) may be made of an impermeable plastic, another material, or combinations thereof. The other side of the reservoir (106) is bounded with another flexible membrane (107) to retain the volatile composition (104) within the reservoir (106) after the volatile container is punctured. While the example of FIG. 1 is described with reference to the reservoir (106) and the volatile container (102) being separated with the flexible membrane (105), any appropriate barriers may be used to retain the volatile composition (104) within the volatile container (102). For example, a rigid plastic may form the section of the volatile container (102) between the activation arm (112) and the volatile composition (104). In such an example, a recess, a weakening in rigid plastic, or other mechanism may lower the force that will break, rupture, or puncture the volatile container (102) and release the volatile composition (104).

A puncturing mechanism (122) is formed in the activation arm (112). In the example of FIG. 1, the puncturing mechanism (122) includes multiple living hinges (124, 126, 128) that separate a first rigid section (130) and a second rigid section (132) of the activation aim (112). An upper living hinge (124) and a lower living hinge (128) are formed facing the volatile container (102) while a middle living hinge (126) is formed facing the wick (110). When the reservoir assembly (100) is inserted into the outer housing, and the first portion (114) of the activation arm (112) engages the interior protrusion (116), the living hinges (124, 126, 128) bend according to the direction that each of the living hinges (124, 126, 128) faces. For example, the middle living hinge (126) faces the wick (110) and thus, bends away from the wick. Likewise, the upper and lower living hinges (124, 128) face the volatile container (102), and thus, bend away from the volatile container (102). As the living hinges (124, 126, 128) bend, the first and second rigid sections (130, 132) pivot towards volatile container (102) until the first and second rigid sections (130, 132) move into the volatile container (102) with a sufficient force to puncture the volatile container (102). As a result, the volatile composition (104) in the volatile container (102) drains into the reservoir (106).

The volatile composition (104) makes contact with the wick (110) which draws in the volatile composition (104) through capillary action to an emanator pad, which will be shown in more detail later, that distributes the volatile composition (104) across the pad's surface area to promote evaporation. The wick (110) is made of any appropriate material that causes aqueous based and/or oil based compositions to be distributed through capillary action. The emanator pad is made of any appropriate material such as porous substrates like porous plastic, paper, fiber, other materials, or combinations thereof. The emanator pad's function is to provide a large surface area from which the volatile composition evaporates.

A removable spacer (134) is positioned between the underside (136) of the first portion (114) of the activation arm (112) and a fitting (138) placed around the wick (110). The removable spacer (134) has a thickness (140) that is sufficient to prevent the bottom (142) of the reservoir assembly (100) from snapping into place within the outer housing. As a result, the reservoir assembly (100) is loosely fitted within the outer housing when the removable spacer (134) is in place. Consequently, a compressive load between the first and second portions (114, 118) of the activation arm (112) is prevented from forming. Thus, while the removable spacer (134) is in place, the puncturing mechanism (122) is prevented from puncturing the volatile container (102) and the reservoir assembly (100) remains in an inactivated state. However, to activate the reservoir assembly (100), the removable spacer (134) is removed so that when the reservoir assembly (100) is inserted into the outer housing, there is a sufficient gap to allow the activation arm (112) to compress as the reservoir assembly (100) is inserted into place within the outer housing.

Figure 2:
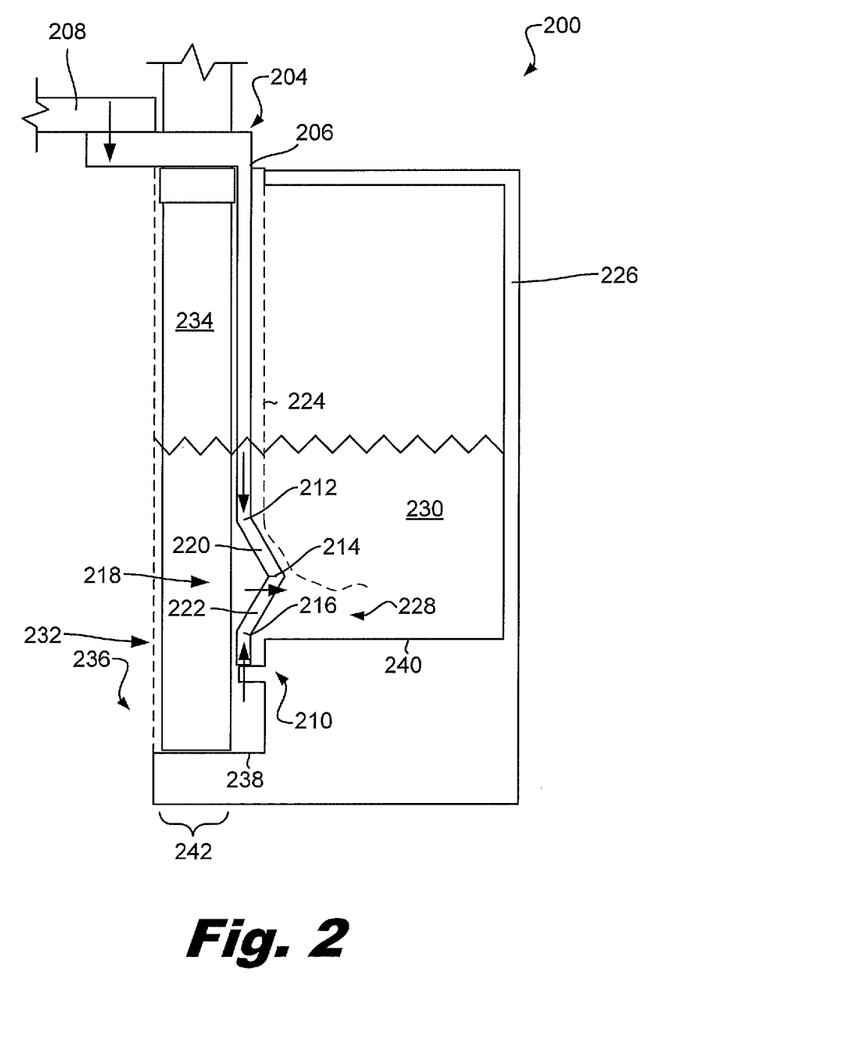
FIG. 2 is a diagram of an example of a reservoir assembly according to the principles described herein.

FIG. 2 is a diagram of an example of a reservoir assembly (200) according to the principles described herein. In this example, the removable spacer is removed from the reservoir assembly (200) which allows the reservoir assembly (200) to be fully inserted into the outer housing. As such, the first portion (204) of the activation arm (206) contacts the interior protrusion (208) of the outer housing, and the reservoir assembly (200) is moved deep enough into the inner chamber of the outer housing that a compressive load is generated between the first and second portions (204, 210) of the activation arm (206). The compressive load is large enough to cause the living hinges (212, 214, 216) of the puncturing mechanism (218) to bend and move the first and second rigid sections (220, 222) laterally towards the flexible membrane (224) of the volatile container (226). The lateral movement of the puncturing mechanism (218) causes the flexible membrane (224) to break or be punctured.

The lateral movement of the puncturing mechanism (218) forms an opening (228) in the volatile container (226) in any appropriate manner. An opening (228) in the flexible membrane (224) may be located at the location where the first and second rigid sections (220, 222) contact the flexible membrane (224). In other examples, the puncturing mechanism (218) causes the opening (228) to be formed elsewhere in the flexible membrane (224). For example, the puncturing mechanism (218) may induce tensile forces throughout the flexible membrane (224) originating at the site of contact that causes the flexible membrane to tear at a weak spot located elsewhere in the flexible membrane (224). In other examples, the first and second rigid sections (220, 222) have a rough surface area, sharp edges, protruding features, or other mechanisms that contribute to forming an opening in the flexible membrane.

The punctured volatile container (226) releases the volatile composition into the remainder of the reservoir's volume where the volatile composition (230) comes into contact with the base end (232) of the wick (234). In the example of FIG. 2, the remainder of the reservoir (236) has a lower floor (238) than a floor (240) of the volatile container (226). The height difference between these floors (238, 240) increases the rate at which the volatile composition (230) drains from the punctured volatile container (226). Also, the remainder of the reservoir (236) has a narrow width (242), which causes the base end (232) of the wick (234) to be submerged deeper into the volatile composition's volume thereby providing a larger contact area between the wick (234) and the volatile composition (230).

Figure 3:
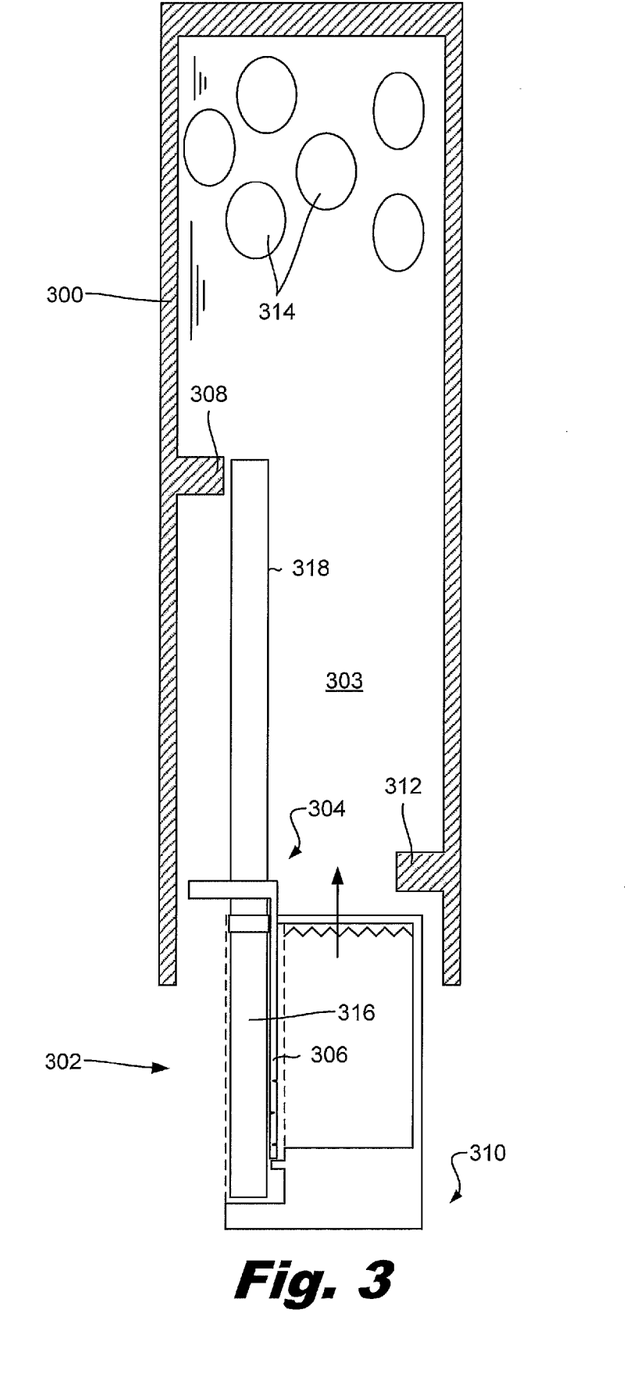
FIG. 3 is a diagram of an example of an outer housing and a reservoir assembly according to the principles described herein.

FIG. 3 is a diagram of an example of an outer housing (300) and a reservoir assembly (302) according to the principles described herein. In this example, the reservoir assembly (302) is partially inserted into an inner chamber (303) of the outer housing (300). The removable spacer is removed from the reservoir assembly (300) thereby allowing a compressive load to be created as the first portion (304) of the activation arm (306) contacts the interior protrusion (308) of the outer housing (300) as a bottom (310) of the reservoir assembly (302) rests on a shelf (312) formed in the inner chamber (303). The shelf (312) may be a single protrusion or multiple protrusions protruding into the inner chamber (303). In other examples, the shelf (312) is a continuous ledge. In yet other examples, a shelf (312) fits into a geometry formed in the reservoir assembly (302) and supports the weight of the reservoir assembly (302) through the geometry. Any appropriate mechanism may be used to secure the reservoir assembly within the outer housing including, but not limited to, snaps, compression fittings, locking mechanisms, bolts, fasteners, other mechanisms, or combinations thereof.

The outer housing (300) has multiple ventilation openings (314) which provide air exposure to the emanator pad's surface area and allows the evaporated volatiles to pass from the inner chamber (303) into the ambient environment outside of the outer housing (300). The ventilation openings (314) may be spaced and shaped to provide an aesthetic look to the outer housing while controlling an amount of air exposure to the emanator pad's surface area.

In some examples, the wick (316) is connected to an emanator pad (318) where the wick provides a transfer mechanism from the drained volatile composition to the emanator pad, and the emanator pad provides the surface area to promote the volatile composition's evaporation. In other examples, the surface area for promoting the volatile composition's evaporation is provided with the shape of the emanator pad (318).

Figure 4:
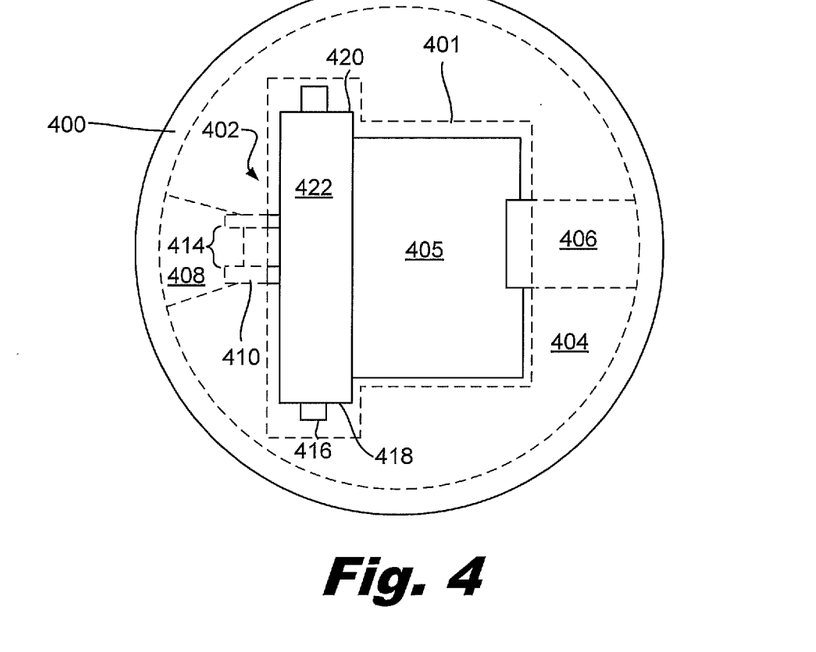
FIG. 4 is a diagram of an example of a bottom view of an outer housing and a reservoir assembly according to the principles described herein.

FIG. 4 is a diagram of an example of a bottom view of an outer housing (400) and a reservoir assembly (402) according to the principles described herein. In this example, the reservoir assembly (402) is inserted into the outer housing (400) through an opening (401) formed in the underside (404) of the outer housing (400). The bottom of the volatile container (405) is resting on the shelf (406) protruding into the outer housing's inner chamber. The interior protrusion (408) is in contact with a first portion (410) of the activation arm. In this example, the first portion (410) has two pieces spaced apart with a gap (414). The gap (414) is large enough to accommodate the width of the wick, which is not visible from the view depicted in the example of FIG. 4. An emanator pad (416) extends over the sides (418, 420) of the reservoir (422). The opening (401) is keyed to allow the reservoir assembly (402) to enter into the outer housing (400) while excluding objects of other shapes from entering.

Figure 5:
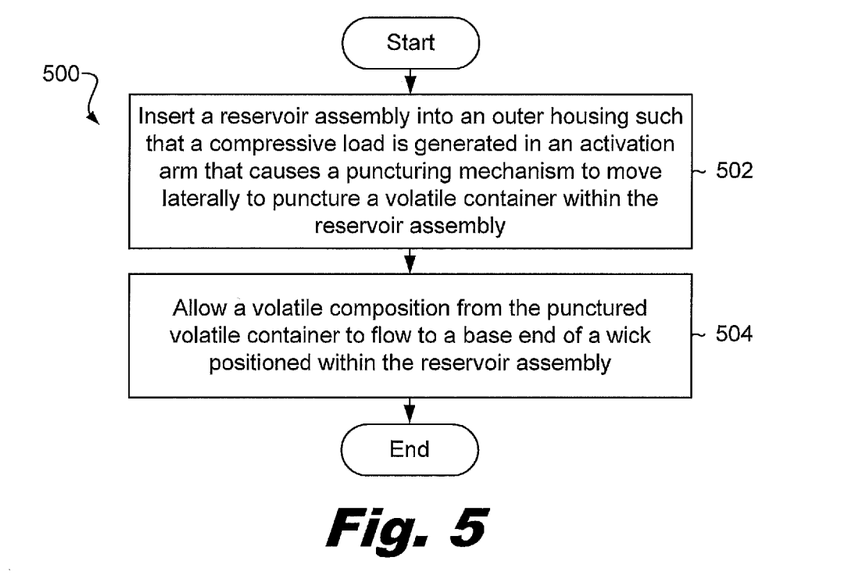
FIG. 5 is a diagram of an example of a method for activating volatile dispensing devices according to the principles described herein.

FIG. 5 is a diagram of an example of a method (500) for activating volatile dispensing devices according to the principles described herein. In this example, the method (500) includes inserting (502) a reservoir assembly into an outer housing such that a compressive load is generated in an activation arm that causes a puncturing mechanism to move laterally to puncture a volatile container within the reservoir assembly, and allowing (504) a volatile composition from the punctured volatile container to flow to a base end of a wick positioned within the reservoir assembly.

In some examples, the method also includes removing a removable spacer that prevents a compressive load from being generated between a first portion and a second portion of the activation arm, which prevents premature activation of the volatile dispensing device during shipping and by the user. The base end of a wick is positioned within the reservoir and a volatile composition from the volatile container comes into contact with the wick when the volatile container is punctured. The wick is made of a material that draws in the volatile composition when the volatile container is punctured and transports the volatile composition to the emanator pad, which distributes the volatile composition across its surface area for evaporation. In other examples, the wick is shaped to provide the surface area that promotes evaporation of the volatile composition.

Figure 6:
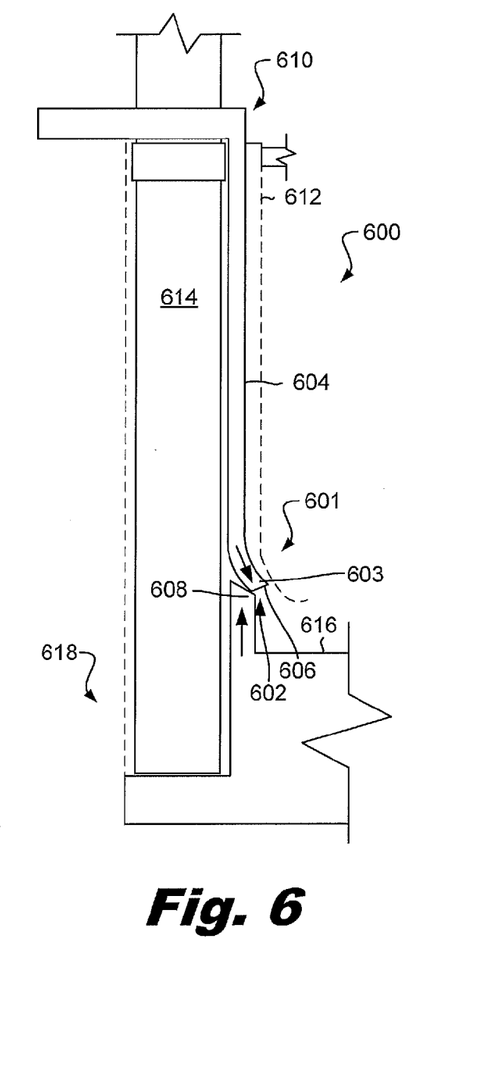
FIG. 6 is a diagram of an example of a reservoir assembly according to the principles described herein.

FIG. 6 is a diagram of an example of a reservoir assembly (600) according to the principles described herein. In this example, the puncturing mechanism (601) includes the second portion (602) of the activation arm (604) having a free end (603) that is shaped with an angle (606). Before activation, the second portion (602) is in contact with a ramp (608). As the first and second portions (610, 602) are compressed together, the angle (606) rides on the ramp (608) which moves the second portion (602) laterally to puncture the flexible membrane (612). The ramp (608) may be incorporated in any appropriate place within the reservoir assembly (600) to move the second portion (602) towards the flexible membrane (612). For example, the ramp (608) may be incorporated on the wick (614), a floor (616) of the reservoir (618), another location, or combinations thereof.

Figure 7:
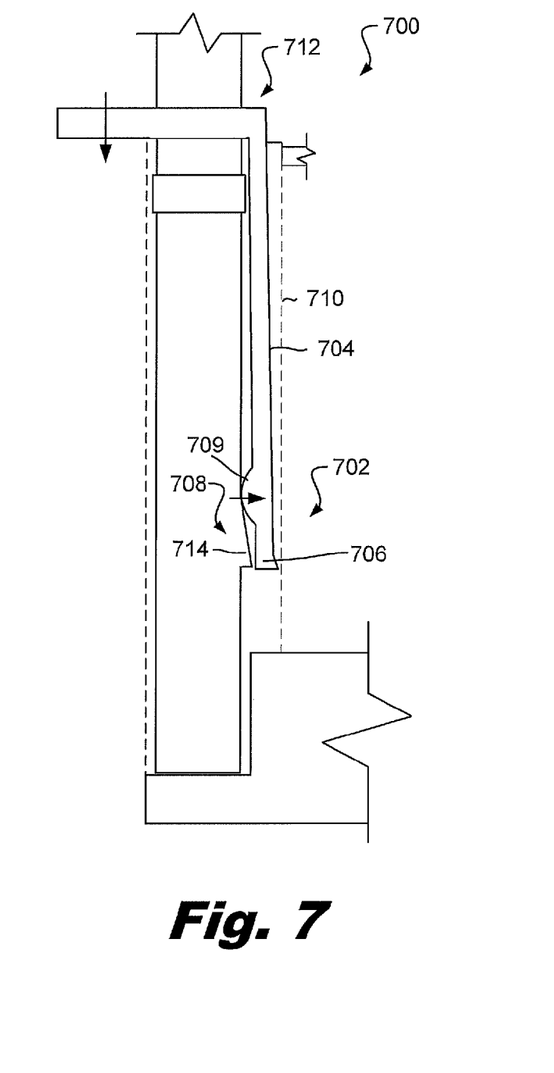
FIG. 7 is a diagram of an example of a reservoir assembly according to the principles described herein.

FIG. 7 is a diagram of an example of a reservoir assembly (700) according to the principles described herein. In this example, the puncturing mechanism (702) includes the activation arm (704) having a free end (706). The second portion (708) of the activation arm (704) includes a protrusion (709) protruding away from the flexible membrane (710). As the first portion (712) of the activation arm (704) is moved downward, the second portion (708) resists the movement when the protrusion (709) contacts a ramp (714). The resistance subjects the activation arm (704) to a compressive load. Some of the compression is relieved by the free end (706) moving laterally towards the flexible membrane (710), which causes the flexible membrane (710) to puncture.

Figure 8:
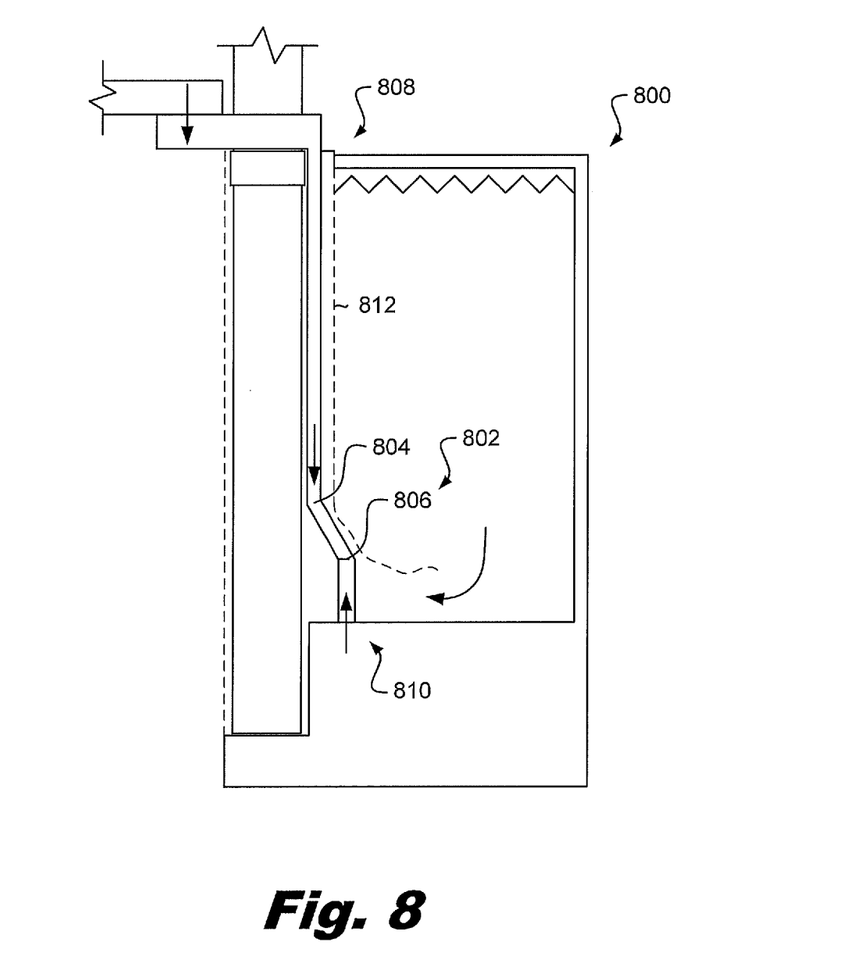
FIG. 8 is a diagram of an example of a reservoir assembly according to the principles described herein.

FIG. 8 is a diagram of an example of a reservoir assembly (800) according to the principles described herein. In this example, the puncturing mechanism (802) includes a first living hinge (804) and a second living hinge (806). As the first and the second portions (808, 810) of the activation arm (812) are compressed together, the living hinges (804, 806) bend. The living hinges (804, 806) are shaped such that the second portion (810) is moved towards the flexible membrane (812) and punctures the flexible membrane (812).

The principles described herein incorporate any appropriate puncturing mechanism that causes lateral movement resulting from compressive forces in the activation arm (812). A non-exhaustive list of features in puncturing mechanisms that are triggered due to a compressive load generated in the activation arm (812) include living hinges, ramps, wedges, other mechanisms, or combinations thereof. In some examples, a single living hinge is used to puncture the flexible membrane. In other examples, more than three living hinges are used to puncture the flexible membrane. In yet other examples, the activation arm (812) buckles under the compressive loads, and the puncturing mechanism includes a weak spot formed in the activation arm (812) that directs how the activation arm (812) buckles such that the flexible membrane is puncture during a buckling event.

Figure 9:
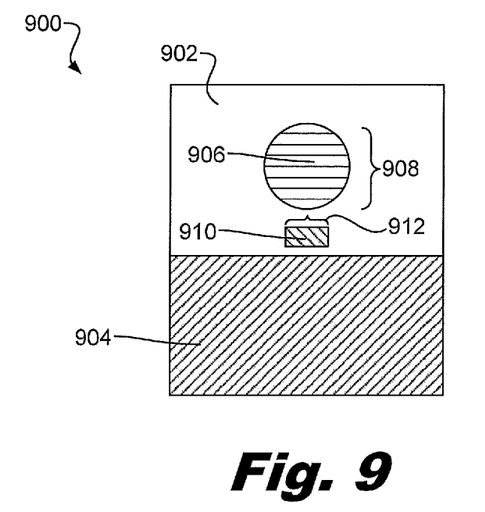
FIG. 9 is a diagram of an example of a top view of a reservoir assembly according to the principles described herein.

FIG. 9 is a diagram of an example of a top view of a reservoir assembly (900) according to the principles described herein. In this example, the reservoir assembly (900) has not been activated yet and has a reservoir (902) and a volatile container (904). A cross section of the wick (906) is depicted as having a circular cross section (908). A cross section of the activation arm (910) is depicted as having a smaller width (912) than the wick (906). In this example, the puncturing mechanism, which is incorporated into the activation arm (910), will contact the volatile container (904) at a location proximate the activation arm (910). While the example in FIG. 9 includes the wick (906) and the activation arm (910) being centered within the reservoir (902), in other examples, the activation arm (910) and/or the wick (906) are off centered.

Figure 10:
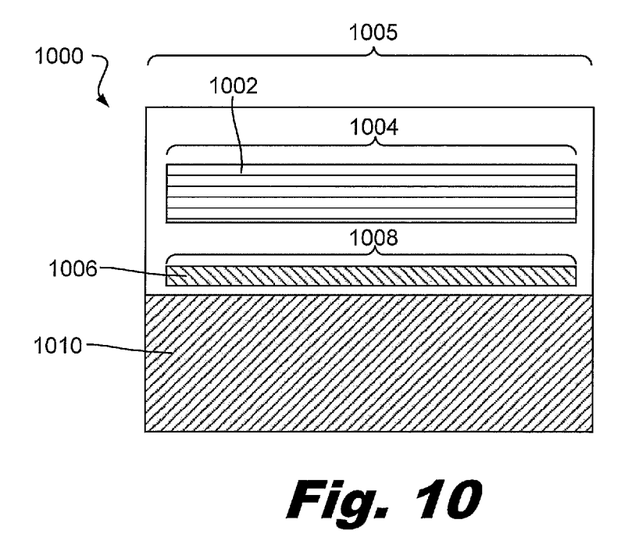
FIG. 10 is a diagram of an example of a top view of a reservoir assembly according to the principles described herein.

FIG. 10 is a diagram of an example of a top view of a reservoir assembly (1000) according to the principles described herein. A cross section of the wick (1002) is depicted as having a long, rectangular cross section (1004) that spans most of the reservoir's width (1005). Also, the cross section of the activation arm (1006) is depicted as having a width (1008) that also spans at least most of the reservoir's width (1005). In this example, the puncturing mechanism, which is incorporated into the activation arm (1006) can contact the volatile container (1010) along the entire width of the activation arm (1006). Thus, the puncture opening formed in the volatile container (1010) as a result of activating the puncturing mechanism may be as large as the activation arm's width. In other examples, multiple puncturing mechanisms are incorporated side by side into the width of the activation arm (1006) such that multiple puncture openings will be formed into the volatile container (1010). In yet other examples, multiple puncturing mechanisms are incorporated into the activation arm (1006) at different heights that will create multiple puncture openings at different heights in the volatile container (1010).

Figure 11:
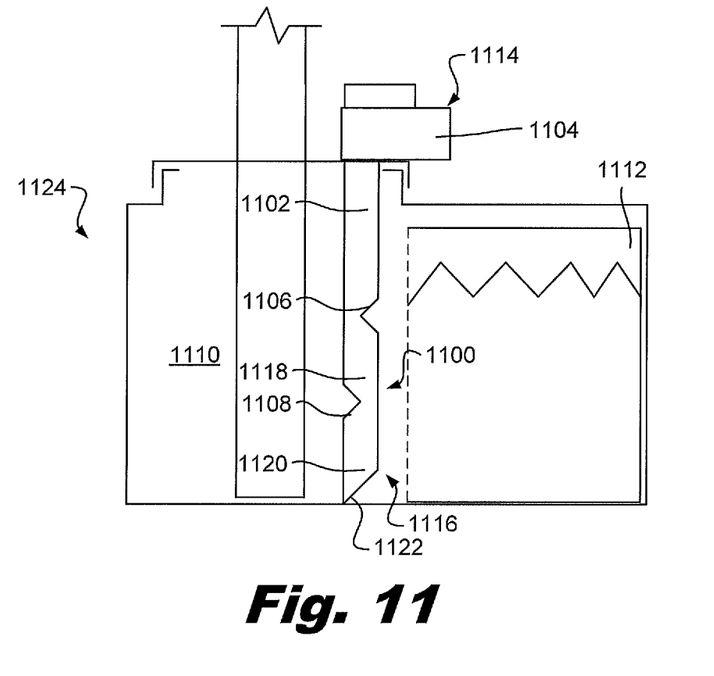
FIG. 11 is a diagram of an example of a puncturing mechanism according to the principles described herein.

FIG. 11 is a diagram of an example of a puncturing mechanism (1100) according to the principles described herein. In this example, the puncturing mechanism (1100) is incorporated into the activation arm (1102) which is prevented from being compressed with the removable spacer (1104). The puncturing mechanism (1100) includes a first living hinge (1106) and a second living hinge (1108) formed activation arm (1102) and residing within a reservoir (1110). The volatile container (1112) is located adjacent to the puncturing mechanism (1100). When the removable spacer (1104) is removed and a first portion (1114) of the activation arm (1100) is pushed towards the second portion (1116) such that a compressive load is generated, the first and the second living hinges (1106, 1108) will bend causing a first rigid segment (1118) and a second rigid segment (1120) to move into and puncture the volatile container (1112). A free end (1122) of the activation arm (1112) is shaped to accommodate the pivoting motion of the second rigid segment (1120) from the generation of the compressive load. The compressive load may be generated as the reservoir assembly (1124) is inserted into an opening of a housing, and the first portion (1114) of the activation arm (1112) contacts a feature within an inner chamber of the housing.

The principles described herein may be used in any appropriate volatile dispensing device. While the above examples have been described with reference to volatile dispensing devices that are air fresheners, any appropriate volatile dispensing device may be used in accordance with the principles described herein. The above description may also be well suited for passive, non-electric devices, such as non-electric continuous action scented oil air fresheners. Other appropriate volatile dispensing devices include devices that dispense fragrances, insecticides, pesticides, insect repellant, animal repellant, other repellants, other volatiles, or combinations thereof.

While the above examples have been described above with reference to specific puncturing mechanisms, any appropriate type of puncturing mechanism according to the principles described herein may be used. Further, while the above examples have been described with reference to specific types of activation arms, any appropriate type, shape, and/or size of activation arm may be used in accordance with the principles described herein. Also, while the above examples have been described with reference to specific types of reservoir assemblies, any appropriate type of reservoir assembly may be used with more or less components in similar or different arrangements than those reservoir assembly described above.

The compressive loads generated to activate the puncturing mechanism may be generated with any appropriate mechanism according to the principles described herein. For example, the compressive load may be generated by inserting the reservoir assembly into the outer housing. In other examples, the compressive load may be generated by pushing the outer housing down over the activation arm. In yet other examples, the activation arm may be part of a wick assembly or other assembly that is inserted into the outer housing separately from the reservoir. In yet other examples, a feature or even the first portion of the activation arm is accessible from outside of the outer housing when the activation arm is secured within the outer housing, and the compressive load is generated through interaction with the accessible feature from outside of the outer housing.

While the examples above have been described with reference to specific outer housings, the outer housing may have any appropriate shape and/or size. For example, the outer housing may have a cylindrical shape, a square shape, a rectangular shape, a symmetric shape, an asymmetric shape, a triangular shape, another shape, or combinations thereof. The ventilation openings in the outer housing may also have any appropriate shape, size, and/or spacing.

While the examples above have been described with reference to specific wick shapes and sizes, any appropriate wick may be used according to the principles described herein. For example, the wick may have a triangular shape, a loop shape, a square shape, a cylindrical shape, another shape, or combinations thereof. The wick may have multiple contact areas with the volatile composition. For example, the wick may have multiple base ends that join to a common emanator pad. Also, the emanator pad may also have surface geometries that increase its surface area and thereby promote an increased rate of evaporation. For example, the surface may have corrugations, dimples, bends, wholes, divots, other surface geometries, or combinations thereof.

Further, the emanator pad can also have multiple panels that are attached to a common wick.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A device for activating a volatile dispensing device, comprising:
 a puncturing mechanism formed between a first portion and a second portion of an activation arm; and
 said puncturing mechanism being shaped to move laterally to puncture a volatile container as a compressive load is applied to said activation arm through said first and second portions, wherein said second portion is positioned within a reservoir between a volatile container and a base portion of a wick, wherein a volatile composition from said volatile container is released into said reservoir upon activation of said puncturing mechanism.

2. A system for activating a volatile dispensing device, comprising:
 a base end of a wick and a volatile container of a volatile composition positioned within a reservoir covered with an outer housing;
 a puncturing mechanism formed between a first portion and a second portion of an activation arm where said first portion is spaced apart from an outer housing with a removable spacer and said second portion is in contact with a floor of said reservoir;
 wherein said puncturing mechanism is shaped to move laterally to puncture said volatile container as a compressive load is applied to said activation arm through said first and second portions when said removable spacer is removed.

3. The system of claim 2, wherein said puncturing mechanism comprises multiple living hinges that collectively bend under a compressive load applied to said activation arm such that at least one rigid section between said multiple living hinges is pivoted towards said volatile container.

4. The system of claim 2, wherein said puncturing mechanism comprises a free end of said activation arm that is positioned to slide laterally as said first and second portions are compressed together.

5. The system of claim 2, wherein said volatile container comprises a section proximate said puncturing mechanism that is made of a flexible membrane.

6. The system of claim 2, wherein said outer housing comprises a shelf to hold said reservoir within an inner chamber of said outer housing, said shelf being spaced apart from an interior protrusion protruding into said inner chamber such that when said reservoir is held with said shelf said interior protrusion causes said compressive load to said activation mechanism.

7. The system of claim 2, wherein said first portion of said activation arm comprises two pieces that form a gap wide enough to fit around a portion of said wick.

8. The system of claim 2, wherein said outer housing comprises at least one ventilation opening to vent airborne chemicals evaporated from said volatile composition from off of a surface area in communication with said wick.

* * * * *